(12) United States Patent
Chen et al.

(10) Patent No.: US 7,405,195 B2
(45) Date of Patent: Jul. 29, 2008

(54) COSMETIC COMPOSITIONS

(75) Inventors: Jidai Chen, Bedford, MA (US);
Yanping Cong, Bedford, MA (US)

(73) Assignee: Natural Beauty Bio-Technology Limited, Taipei (TW)

( * ) Notice: Subject to any disclaimer, the term of this patent is extended or adjusted under 35 U.S.C. 154(b) by 0 days.

(21) Appl. No.: 11/391,692

(22) Filed: Mar. 27, 2006

(65) Prior Publication Data

US 2007/0224139 A1 Sep. 27, 2007

(51) Int. Cl.
*A61K 38/16* (2006.01)
(52) U.S. Cl. ......................................................... 514/2
(58) Field of Classification Search .................. None
See application file for complete search history.

(56) References Cited

U.S. PATENT DOCUMENTS

| | | | |
|---|---|---|---|
| 5,614,489 A | 3/1997 | Mohammadi et al. | |
| 5,709,864 A | 1/1998 | Andre et al. | |
| 6,306,848 B1 | 10/2001 | Fujimura et al. | |
| 6,551,604 B1 | 4/2003 | Beck et al. | |
| 6,989,435 B2 * | 1/2006 | Grainger et al. | 530/328 |
| 2003/0113393 A1 * | 6/2003 | Babish et al. | 424/778 |

* cited by examiner

*Primary Examiner*—Cecilia J. Tsang
*Assistant Examiner*—Christina M. Bradley
(74) *Attorney, Agent, or Firm*—Occhiuti Rohlicek & Tsao LLP

(57) ABSTRACT

A topical composition having (i) an isolated polypeptide having the sequence of SEQ ID NO: 1 or a functional equivalent thereof, and (ii) a cosmetically acceptable carrier; and use thereof.

10 Claims, No Drawings

COSMETIC COMPOSITIONS

BACKGROUND

Aging is a natural process not yet totally understood. It appears to be genetically controlled and can be accelerated by environmental, dietary, and pathological factors. At the cellular or molecular level, aging is considered as the result of the inability of an organism to respond adaptively to environmental changes. As people age, the process of self-renewal or replacement of skin cells slows down.

The skin has three layers: the epidermis, the dermis, and the hypodermis. The epidermis, the outmost layer, is filled with strata of specialized skin cells known as keratinocytes. These cells start out in the deepest layer of the epidermis and migrate to the skin surface. During this process, they lose moisture and are eventually sloughed off. In young people, this process takes about 4 weeks to travel to the surface. In people of age over 50, it can take about 5.5 weeks. The dermis, the layer beneath the epidermis, contains blood vessels that nourish the skin cells and the structural elements e.g., collagen and elastin, which keep the skin firm and springy. Aging results in fewer keratinocyte layers and, thus, less skin stem cell self-renewal and replacement. Also, the aged skin lost collagen and elastin poorly, leading to thin and papery-look appearance. Consequently, wrinkles form. This slow, concurrent losses of dermal cellular and structural elements, thickness, and elasticity, together with wrinkle and segment formation, are the most obvious indicators of skin aging.

Various compositions and methods have been used for regulating undesirable skin surface texture, such as fine lines, wrinkles, pores, and the like. However, many of them are ineffective or cause allergy and other side effects. Thus, there is a need for a more effective and safer cosmetic composition.

SUMMARY

This invention relates to cosmetic compositions and use thereof. Accordingly, one aspect of this invention features a topical composition containing an isolated polypeptide having the sequence of stromal-derived factor-1 (SDF-1) variant named stem cell active factor (SCAF) or its functional equivalent, and a cosmetically acceptable carrier. Shown below are the polypeptide sequence of SCAF and its cDNA sequence (SEQ ID NOs: 1 and 2, respectively)

```
MNAKVVVVLVLVLTALCLSDGKPVSLSYRCPCRFFESHVARANVKHLKILNTPNCALQI  (SEQ ID NO: 1)

VARLKNNNRQVSIDPKLKWIQEYLEKALNK

ATGAACGCCAAGGTCGTGGTCGTGCTGGTCCTCGTGCTGACCGCGCTCTGCCTCAGCGA  (SEQ ID NO: 2)

CGGGAAGCCCGTCAGCCTGAGCTACAGATGCCCATGCCGATTCTTCGAAAGCCATGTTG

CCAGAGCCAACGTCAAGCATCTCAAAATTCTCAACACTCCAAACTGTGCCCTTCAGATT

GTAGCCCGGCTGAAGAACAACAACAGACAAGTGTCCATTGACCCGAAGCTAAAGTGGAT

TCAGGAGTACCTGGAGAAAGCTTTAAACAAGTAA
```

An "isolated polypeptide" refers to a polypeptide that has been separated from other proteins, lipids, and nucleic acids with which it is naturally associated. The polypeptide can constitutes at least 10% (i.e., any percentage between 10% and 100%) by dry weight of the purified preparation. Purity can be measured by any appropriate standard method, for example, by column chromatography, polyacrylamide gel electrophoresis, or HPLC analysis. An isolated polypeptide of the invention can be purified from a natural source, produced by recombinant DNA techniques, or by chemical methods. A "functional equivalent" refers to a polypeptide derivative of the SCAF polypeptide, e.g., a protein having one or more point mutations, insertions, deletions, truncations, a fusion protein, or a combination thereof. It retains substantially the activity of the SCAF polypeptide, i.e., the ability to improve skin condition (e.g., reducing wrinkles). The isolated polypeptide can contain SEQ ID NO: 1 or a functional fragment of SEQ ID NO: 1. In general, the functional equivalent is at least 75% (e.g., any number between 75% and 100%, inclusive) identical to SEQ ID NO: 1. A "cosmetically acceptable" or "dermatologically-acceptable" composition or component refers a composition or component that is suitable for use in contact with human skin without undue toxicity, incompatibility, instability, allergic response, and the like.

The above-described topical composition can further contain an agent selected from the group consisting of an anti-wrinkle herbal extract, a whiting herbal extract, and an anti-acne herbal extract. Examples of the anti-wrinkle herbal extract include a hop extract, a horsetail extract, or both. The whiting herbal extract can contain a *Scutellaria baicalensis* root extract, a *Saxifrage sarmentosa* root extract, or both. Examples of the anti-acne herbal extract includes a watercress extract, a witch hazel extract, a centella extract, a licorice extract, or a combination thereof. The topical composition can further contain a pure polysaccharide, e.g., L-fucose, D-galactose, galacturonic acid, or a combination thereof.

The topical composition of the invention provides an essentially immediate improvement in skin feel and appearance. It is also useful for providing visual improvements in skin appearance or conditions following multiple topical applications. Further, the composition provides the visual benefits without imparting an unacceptable skin appearance.

Thus, the invention also features a method of reducing skin wrinkles or promoting hair growth. The method includes applying to a surface of skin in need thereof a safe and effective amount of the above-described topical composition. A safe and effective amount refers to an amount of a compound, component, or composition sufficient to significantly induce a positive benefit, preferably a positive skin appearance or feel benefit, including independently the benefits disclosed herein, but low enough to avoid serious side effects, i.e., to provide a reasonable benefit to risk ratio, within the scope of sound medical judgment.

The invention features an isolated polypeptide containing the above-listed SEQ ID NO: 1 and an isolated nucleic acid that contains a sequence encoding the polypeptide, e.g., SEQ ID NO: 2. The polypeptide can be used in the composition described above A nucleic acid refers to a DNA molecule (e.g., a cDNA or genomic DNA), an RNA molecule (e.g., an mRNA), or a DNA or RNA analog. A DNA or RNA analog can be synthesized from nucleotide analogs. The nucleic acid molecule can be single-stranded or double-stranded, but preferably is double-stranded DNA. An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. The nucleic acid described above can be used to express the polypeptide of this invention. For this purpose, one can operatively linked the nucleic acid to suitable regulatory sequences to generate an expression vector.

A vector refers to a nucleic acid molecule capable of transporting another nucleic acid to which it has been linked. The vector can be capable of autonomous replication or integrate into a host DNA. Examples of the vector include a plasmid, cosmid, or viral vector. The vector of this invention includes a nucleic acid in a form suitable for expression of the nucleic acid in a host cell. Preferably the vector includes one or more regulatory sequences operatively linked to the nucleic acid sequence to be expressed. A "regulatory sequence" includes promoters, enhancers, and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vector can be introduced into host cells to produce the polypeptide of this invention. Also within the scope of this invention is a host cell that contains the above-described nucleic acid. Examples include *E. coli* cells, insect cells (e.g., using baculovirus expression vectors), yeast cells, or mammalian cells. See e.g., Goeddel, (1990) Gene Expression Technology: Methods in Enzymology 185, Academic Press, San Diego, Calif. To produce a polypeptide of this invention, one can culture a host cell in a medium under conditions permitting expression of the polypeptide encoded by a nucleic acid of this invention, and purify the polypeptide from the cultured cell or the medium of the cell. Alternatively, the nucleic acid of this invention can be transcribed and translated in vitro, for example, using T7 promoter regulatory sequences and T7 polymerase.

The details of one or more embodiments of the invention are set forth in the description below. Other features, objects, and advantages of the invention will be apparent from the description and from the claims.

DETAILED DESCRIPTION

This invention is based, at least in part, on unexpected findings that a topical composition containing SCAF regulates and improves aging skin conditions. As mentioned above, the principal process of aging take place both in the top layers of skin (i.e. the epidermis) and in the dermis. A composition of this invention not only regulates and improves the conditions of the epidermis, but also effects the dermis by improving the nourishment and activating stem cells to renew and differentiate into fibroblasts, keratinocytes, and other cellular components of the skin.

SCAF, an SDF-1 variant, described herein is a member of a chemokine family consisting of small secreted proteins (8-12 kDa). This family of chemokines are known to cause activation and migration of leukocytes (Baggiolini, 1998, Nature 392, 565-8; and Murdoch et al., 2000, Blood 95, 3032-43). As described in the examples below, a composition of this invention unexpectedly improves the condition of the epidermis layer or hair growth, without causing side effects related to leukocyte activation and migration, such as allergy. Thus, SCAF and other SDF-1 variants can be used as an active ingredient in a cosmetic composition.

While many SDF-1 preparations can be used, highly purified SDF-1 is preferred. Examples of SDF-1 include mammalian SDF-1 (e.g., human SDF-1) or SDF-1 having substantially the same biological activity as mammalian SDF-1. All of naturally occurring SDF-1, genetic engineered SDF-1, and chemically synthesized SDF-1 can be used. SDF-1 obtained by recombinant DNA technology may have the same amino acid sequence as naturally a occurring SDF-1 (SEQ ID NO: 1) or an functionally equivalent thereof. The term "SDF-1" also covers chemically modified SDF-1. Examples of chemically modified SDF-1 include SDF-1 subjected to conformational change, addition or deletion of a sugar chain, and SDF-1 to which a compound such as polyethylene glycol has been bound. Once purified and tested by standard methods or according to the method described in the examples below, SDF-1 can be included in a topical composition.

The amino acid composition of the SDF-1 polypeptide described herein may vary without disrupting the ability of the polypeptide to improve skin condition. For example, it can contain one or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in SEQ ID NO: 1 is preferably replaced with another amino acid residue from the same side chain family. Alternatively, mutations can be introduced randomly along all or part of SEQ ID NO: 1, such as by saturation mutagenesis, and the resultant mutants can be screened for the ability to improve skin condition to identify mutants that retain the activity as descried below in Example 3.

A polypeptide of the invention can be obtained as a synthetic polypeptide or a recombinant polypeptide. To prepare a recombinant polypeptide, a nucleic acid encoding it can be linked to another nucleic acid encoding a fusion partner, e.g., glutathione-s-transferase (GST), 6x-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide of this invention.

The topical composition of this invention can further contain an anti-wrinkle herbal extract, a whiting herbal extract, or an anti-acne herbal extract. An extract is a concentrated preparation of the essential constituents of a medicinal herb. Typically, the essential constituents are extracted from a herb by suspending the herb in an appropriate choice of solvent, typically, water, ethanol/water mixture, methanol, butanol, iso-butanol, acetone, hexane, petroleum ether or other suitable organic solvents. The extracting process may be further facilitated by means of maceration, percolation, repercolation, counter-current extraction, turbo-extraction, or by carbon-dioxide hypercritical (temperature/pressure) extraction. After filtration to rid of herb debris, the extracting solution may be further evaporated and thus concentrated to yield a soft extract (extractum spissum) or eventually a dried extract (extracum siccum), by means of spray drying, vacuum oven drying, fluid-bed drying, or freeze-drying. The soft extract or dried extract may be further dissolved in a suitable liquid to a desired concentration for administering or processed into a suitable form.

In a 100 g topical composition of this invention, exemplary quantities of the herb extract ingredients are: the anti-wrinkle herbal extract 3-30 g (e.g., 15 g); the whiting herbal extract, 3-30 g (e.g., 15 g); the anti-acne herbal extract: 3-30 g (e.g., 15 g); and SDF-1 2000-5000 Unit (e.g., 3000 unit). One "Unit" is defined as the amount of SDF-1 that, after administered to a subject, induce the migration of $1\times10^6$ peripheral blood cells for at least 3 mm in vitro. The anti-wrinkle herbal extract can be prepared from hop or horsetail; the whiting herbal extract can be obtained from *Scutellaria baicalensis* root, or *Saxifrage sarmentosa* root; and the anti-acne herbal extract can be obtained from watercress, witch hazel, centella extract, or licorice. These herbs are commercially available. After authenticating each herb, conventional methods may be used to process the composition of the present invention into a form suitable for administering to human subjects. Those methods are either described in pertinent literature or commonly used by practitioners of herbal medicine.

The composition of the present invention also contains a safe and effective amount of a dermatologically acceptable carrier that is suitable for topical application to the skin. It enables the essential materials and optional components in it to be delivered to the skin at an appropriate concentration. The carrier can thus act as a diluent, dispersant, solvent, or the like to ensure that the active materials are applied to and distributed evenly over the selected target at an appropriate concentration. The carrier can be solid, semi-solid, or liquid. Preferably, the carrier is in the form of a lotion, a cream, or a gel, more preferably one that has a sufficient thickness or yield point to prevent the active materials from sedimenting. The carrier can itself be inert or it can possess dermatological benefits of its own. The carrier should also be physically and, chemically compatible with the essential components described herein, and should not unduly impair stability, efficacy, or other use benefits associated with the compositions of the present invention.

The type of carrier utilized in the present invention depends on the type of product form desired for the composition. The topical compositions useful in the subject invention may be made into a wide variety of product forms such as are known in the art. These include, but are not limited to, lotions, creams, gels, sticks, sprays, ointments, pastes, and mousses. These product forms may comprise several types of carriers including, but not limited to, solutions, aerosols, emulsions, gels, solids, and liposomes.

Preferred carriers can contain a dermatologically acceptable, hydrophilic diluent. Suitable hydrophilic diluents include water, organic hydrophilic diluents, such as $C_1$-$C_4$ monohydric alcohols and low molecular weight glycols and polyols (including propylene glycol, polyethylene glycol of, e.g., MW 200-600), polypropylene glycol of, e.g. MW 425-2025, glycerol, butylene glycol, 1,2,4-butanetriol, sorbitol esters, 1,2,6-hexanetriol, ethanol, iso-propanol, sorbitol esters, ethoxylated ethers, propoxylated ethers, and combinations thereof. The composition preferably comprises at least about 60% of the hydrophilic diluent.

Preferred carriers also contain an emulsion having a hydrophilic phase, especially an aqueous phase, and a hydrophobic phase e.g., a lipid, oil, or oily material. As well known to one skilled in the art, the hydrophilic phase will be dispersed in the hydrophobic phase, or vice versa, to form respectively hydrophilic or hydrophobic dispersed and continuous phases, depending on the composition ingredients. The term "dispersed phase," a term well-known to one skilled in the art, refers to a phase that exists as small particles or droplets suspended in and surrounded by a continuous phase. The dispersed phase is also known as the internal or discontinuous phase. The emulsion may be or contain (e.g., in a triple or other multi-phase emulsion) an oil-in-water emulsion or a water-in-oil emulsion such as a water-in-silicone emulsion. Oil-in-water emulsions typically comprise from about 1% to about 50% (preferably about 1% to about 30%) of the dispersed hydrophobic phase and from about 1% to about 99% (preferably from about 40% to about 90%) of the continuous hydrophilic phase; water-in-oil emulsions typically comprise from about 1% to about 98% (preferably from about 40% to about 90%) of the dispersed hydrophilic phase and from about 1% to about 50% (preferably about 1% to about 30%) of the continuous hydrophobic phase. The emulsion may also comprise a gel network, such as described in G. M. Eccleston, Application of Emulsion Stability Theories to Mobile and Semisolid O/W Emulsions, Cosmetics & Toiletries, Vol. 101, November 1996, pp. 73-92, incorporated herein by reference. Preferred compositions herein are oil-in-water emulsions.

Preferred examples of the topical composition of this invention have an apparent viscosity of from about 5,000 to about 200,000 mPa·s (centipoise). For example, preferred lotions have an apparent viscosity of from about 10,000 to about 40,000 mPa·s; preferred creams have an apparent viscosity of from about 30,000 to about 160,000 mPa·s. Apparent viscosity can be determined using a Brookfield DVII RV viscometer, spindle TD, at 5 rpm, or the equivalent thereof. The viscosity is determined on a composition after the composition has been allowed to stabilize following its preparation, generally at least 24 hours under conditions of 25° C.±1° C. and ambient pressure after preparation of the composition. Apparent viscosity is measured with the composition at a temperature of 25° C.±1° C., after 30 seconds spindle rotation.

The topical composition of the present invention is usually formulated to have a pH of 9.5 or below and in general have a pH in the range from about 4.5 to about 9, more preferably from about 5 to about 8.5. Some examples, particularly those containing an additional active agent such as salicylic acid, require a lower pH in order for the additional active to be fully efficacious. These compositions are usually formulated to have a pH of from about 2.5 to about 5, more preferably from about 2.7 to about 4.

The topical compositions may contain a wide variety of optional components, provided that such optional components are physically and chemically compatible with the essential components described herein, and do not unduly impair stability, efficacy, or other use benefits associated with the compositions. Optional components may be dispersed, dissolved, or the like in the carrier of the present compositions.

Exemplary optional components include emollients, oil absorbents, antimicrobial agents, binders, buffering agents, denaturants, cosmetic astringents, external analgesics, film formers, humectants, opacifying agents, perfumes, pigments, skin soothing and healing agents, preservatives, propellants, skin penetration enhancers, solvents, suspending agents, emulsifiers, cleansing agents, thickening agents, solubilising agents, waxes, sunscreens, sunless tanning agents, antioxidants and/or radical scavengers, chelating agents, anti-acne agents, anti-inflammatory agents, desquamation agents/exfoliants, organic hydroxy acids, vitamins, and natural extracts. Examples of such materials are described in Harry's Cosmeticology, 7th Ed., Harry & Wilkinson (Hill Publishers, London 1982); in Pharmaceutical Dosage Forms—Disperse Systems; Lieberman, Rieger & Banker, Vols. 1 (1988) & 2 (1989); Marcel Decker,. Inc.; in The Chemistry and Manufacture of Cosmetics, 2nd. Ed., deNavarre (Van Nostrand 1962-1965); and in The Handbook of Cosmetic Science and Technology, 1st Ed. Knowlton & Pearce (Elsevier 1993) can also be used in the present invention.

The topical composition of the present invention is generally prepared by conventional methods such as are known in the art of making topical compositions. Such methods typically involve mixing of the ingredients in one or more steps to a relatively uniform state, with or without heating, cooling, application of vacuum, and the like.

The topical composition is useful for regulating or improving skin condition, including regulating visible or tactile wrinkles or discontinuities in skin, e.g., visible and/or tactile wrinkles or discontinuities in skin texture or color, more especially those associated with skin ageing. Such wrinkles or discontinuities may be induced or caused by internal factors (e.g., chronological aging and other biochemical changes from within the skin) or external factors (e.g., ultraviolet radiation, environmental pollution, wind, heat, low humidity, harsh surfactants, and abrasives).

Regulating skin conditions can be carried out prophylactically or therapeutically. Prophylactical regulation includes delaying, minimizing, or preventing visible or tactile wrinkles or discontinuities in skin. Therapeutic regulation, on the other hand, includes ameliorating, diminishing, minimizing or effacing such wrinkles or discontinuities. Regulating skin conditions involves improving skin appearance feel, e.g., providing a smoother, more even appearance, or feel and reducing signs of aging.

To use a topical composition of this invention, one can topically apply to the skin a safe and effective amount of the composition. The applied amount, the frequency of application and the period of use vary widely depending upon the active levels of a given composition and the level of regulation desired, e.g., in light of the level of skin ageing present in the subject and the rate of further skin ageing.

A wide range of quantities of the compositions of the present invention can be employed to provide a skin appearance and/or feel benefit. Quantities of the compositions typically applied per application are from about 0.1 mg/cm$^2$ to about 10 mg/cm$^2$, e.g., 2 mg/cm$^2$. Typically, a composition can be used once per day. However application rates can vary from about once per week up to about three times per day or more.

The topical compositions of this invention provides a visible improvement in skin condition essentially immediately following application of the composition to the skin. Such immediate improvement involves coverage or masking of skin imperfections such as textural discontinuities (including those associated with skin aging, e.g., enlarged pores), or providing a more even skin tone or color. The compositions of the invention also provide visible improvements in skin condition following chronic topical application. "Chronic topical application" involves continued topical application of a composition over an extended period during the subject's lifetime, preferably for a period of at least about one week, one month, three months, six months, or one year. Chronic regulation of skin condition involves improvement of skin condition following multiple topical applications.

Regulating skin conditions is preferably performed by applying a composition in the form of a skin lotion, cream, cosmetic, or the like which is intended to be left on the skin for an extended period for some aesthetic, prophylactic, therapeutic or other benefit (i.e., a "leave-on" composition). As used herein, "leave-on" compositions exclude rinse-off skin cleansing products. After applying the composition to the skin, the leave-on composition is preferably left on the skin for a period of at least about 15 minutes, 30 minutes, 1 hour, or up to about 12 hours.

The specific examples below are to be construed as merely illustrative, and not limitative of the remainder of the disclosure in any way whatsoever. Without further elaboration, it is believed that one skilled in the art can, based on the description herein, utilize the present invention to its fullest extent.

EXAMPLE 1

A number of extracts were prepared from herb plants. In general, fresh plants were used to prepare extracts based on the principle defined in the German Homeopathic Pharmacopoeia (HAB 1/78). Fresh plants should be collected or harvested in dry whether and be as free of dust or dirt as possible. The plants must have no external sign of disease and must have not withered or dead parts, major injuries, rot, or other changes not inherent in the species. If necessary, the plants should be washed with as little water as possible. The plants should then processed immediately. Unless specified otherwise, the following harvesting times should be observed:

| Harvested target | Harvesting time |
| --- | --- |
| Whole plants (including underground parts) | When in flower |
| Herbs (excluding underground parts and including leaves and shoots) | After complete development, shortly before or at start of blossoming |
| Blossom | Shortly after opening |
| Barks | Autumn or spring |
| Roots and root stocks | Annuals, when seeds are ripe; perennials, spring |
| Fruits and seeds | When ripe |
| Unripe fruits | Before ripening |
| Mushrooms | After complete development of fruiting body |

After harvesting, the plants or plant parts were cleaned, crushed, and extracted in a solvent, such as propylene glycol/ethanol or ethanol.

A hop extract was obtained using a solvent of water, propylene glycol, and ethanol (43%, 42%, and 15%, respectively). The resultant extract was a brown-yellow liquid with an aromatic odor, a sweetish-bitter taste, a pH value of 4.4-5.5, and a density of 1.000-1.0015 g/ml. It was soluble in water, 60% ethanol, or 94% ethanol.

A horsetail extract was prepared from *Equisetum arvense* using the just-mentioned solvent. The extract was a yellow liquid with a sweetish-bitter taste, no odor, a pH value of 5.5-6.5, and a density of 1.000-1.0015 g/ml. The extract was soluble in water and 60% ethanol, but formed a slightly opalized solution in 94% ethanol. Active ingredients in this extract included silicic acid, saponin, and flavonoids.

A *Scutellaria baicalensis* root extract was prepared using ethanol from the root of *Scutellaria baicalensis* Georgi (labiatae). Before extracting, the periderm was removed in 50% 1,3-butylene glycol solution by heating, refluxing, and filtering. The resulting filtrate was concentrated to 1/20 in volume and extracted with pure water. The mixture was then mixed with the same volume of 1,3-butylene glycol and filtered. The filtrate retained was a yellowish brown clear liquid with a characteristic odor.

A *Saxifrage sarmentosa* root extract was prepared from *Saxifraga stolonifera* Meerburg (Saxifragaceae) using 1,3-butylene glycol. *Saxifrage sarmentosa* roots were cut into pieces and mixed with 30 v/v % 1,3-butylene glycol (120 litter for 10 kg *Saxifrage sarmentosa*). The resultant mixture was filtered to obtain a clear, brown liquid, which had a pH value of 4.0-6.0 and a density of 1.0100 to 1.0300 g/ml.

A watercress extract was obtained from *Nasturtium officinal* using two volumes of a solvent containing water, propylene glycol, and ethanol (43%, 42%, and 15%, respectively). The extract thus obtained was soluble in water, 60% ethanol, or 94% ethanol. It had a density of 1,000-1.010 g/ml and a pH value of 5.0-6.0. Active ingredients in this extract included mustard glycosides, gluconasturtiine, etheric oils, and raphanol.

A witch hazel extract was prepared from the leaves of *Hamamelis virginiana* also using the just-mentioned solvent containing water, propylene glycol, and ethanol. The resultant extract was a brown-yellow liquid with a characteristic aromatic odor, a sweetish taste, a pH value of 4.0-5.0, and a density of 1.0100-1.0250 g/ml.

A centella extract was prepared using 1:1 ethanol and water in the same manner described above.

To prepare a licorice extract, finely cut licorice roots were extracted with cold water. Ethanol was then added to the extract. The precipitate was retained by sedimentation and mixed with inorganic acid. The resulting mixture was filtrated. After neutralizing. The mixture was dissolved in an ammonium solution and evaporated to dry. The remain was re-crystallized in acetic acid or ethanol. The licorice extract (containing monoammonium glycyrrhizinate) thus-obtained was a white to yellowish crystal powder with a characteristic odor and sweet taste.

EXAMPLE 2

The coding sequence of the human SCAF gene was cloned into a retroviral expression vector and placed under the control of a CMV promoter. A sequence encoding a truncated NGFR protein was also cloned into the vector and placed under the control of the retroviral LTR. The NGFR protein was used as a selective marker. All of the constructs were identified by restriction enzyme digestion and confirmed by DNA sequencing analysis. A confirmed vector was transfected into mammalian cells to express the SCAF protein.

Expressed SCAF protein was purified by standard procedure, sterilized by membrane filtration (pore-size of 0.2 μm), and diluted in PBS to form a SCAF-containing composition. The SCAF and the extracts described in Example 1 above were used to prepare a topical composition according to the following recipe:

TABLE 1

| Ingredients | w/w (%) |
|---|---|
| Wheat Germ Oil | 2.5 |
| Jojoba Oil | 3.5 |
| Biosaccharide Gum-1 | 5 |
| Anti-Wrinkle herbal blend | 15 |
| Whitening herbal blend | 15 |
| Anti-acne herbal blend | 15 |
| Glycerin | 6 |
| 1,3 Butylene Glycol | 5 |
| Sorbtiol | 5 |
| Polysorbate 85 | 2 |
| Xanthan Gum | 0.5 |
| Methylcellulose | 0.25 |
| Methylparaben | 0.1 |
| Proylparaben | 0.1 |
| SDF-1 | 3000 Unit |
| Purified water | Add to 100 g |

EXAMPLE 3

The safety of a SCAF-containing composition was tested in an animal model for allergy and other adverse effects.

Female hairless SKH-1 mice, 6-8 weeks old were used. Such mice have been widely used for evaluating the safety of a skin protection agent. More specifically, 12 hairless SKH-1 mice were divided into two groups: Control group and Experimental group (6 in each). The mice in the Control group were administered with PBS; and the mice in the Experimental group were treated with the SCAF composition at 20 times of the working concentration as described in Table 1 above (3000 U/100 g). The PBS or SCAF composition was smeared onto a circled skin area in the flank of each mouse twice per day for 3 months. During this period, each mouse was observed for behaviors indicating allergy or toxicity (e.g., uneasiness and scratching) and changes in the body temperature.

All mice survived the 3-month period and showed no change of behaviors during this period. The body temperature of each mouse remained in a normal range. Gross skin examination indicated no obvious abnormalities, such as edema, redness of skin, or neoplasm.

At the end of the $1^{st}$ or $2^{nd}$ month, a skin sample was obtained from each mouse by biopsy. At the end of the $3^{rd}$ month, all mice were sacrificed by euthanasia and a skin sample was obtained from each by autopsy. Each sample was then subjected to Haematoxylin & Eosin staining and examined under a microscope for any obvious abnormality, such as neoplasm, changes in skin structure and morphology, allergy reaction, and others. No abnormality was found in the epidermis (stratum corneum, granulosum, malpighii, and basale), the dermis, and the subcutaneous tissue. The above results demonstrate that the SCAF-containing composition is safe and does not cause allergy or other adverse effects to the skin.

The above-described SCAF-containing composition was tested on human volunteers. Each person was smeared with 0.9% NaCl solution on one arm, and the SCAF-containing composition on the other arm (15 time of the working concentration) twice a day for 3 weeks. The results are shown in Table 2. The experiment was repeated on another group of human volunteers except that a SCAF-containing composition of 10 time of the working concentration was used twice a day for 2 weeks. The results are shown in Table 3.

TABLE 2

| Volunteer | Person | Age Range | Allergy | Other Symptoms |
|---|---|---|---|---|
| Male | 12 | 25-58 | 0 | 1* |
| Female | 18 | 22-52 | 0 | 0 |

*One volunteer had a very light scratch on the tested area during the testing period. The skin showed a short term redness, but recovered shortly.

TABLE 3

| Volunteer | Person | Age Range | Allergy | Other Symptoms |
|---|---|---|---|---|
| Male | 8 | 33-55 | 0 | 0 |
| Female | 18 | 28-48 | 0 | 0 |

The results demonstrate that the SCAF-containing composition does not cause allergy or other adverse effects to human skin.

The above experiment was repeated using the composition described above in Table 1. No allergy or other adverse effects were found.

Further, the composition was tested for its wrinkle-reducing efficacy. More specifically, 32 volunteer female subjects of 25-55 years old were administered with the composition for 30 days. All of them showed visible reducing in wrinkle.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A topical composition comprising an isolated polypeptide having the sequence of SEQ ID NO: 1 and a cosmetically acceptable carrier.

2. The topical composition of claim 1, further comprises an agent selected from the group consisting of an anti-wrinkle herbal extract, a whiting herbal extract, and an anti-acne herbal extract.

3. The topical composition of claim 2, wherein the anti-wrinkle herbal extract contains a hop extract, a horsetail extract, or both.

4. The topical composition of claim 2, wherein the whiting herbal extract contains a *Scutellaria baicalensis* root extract, a *Saxifrage sarmentosa* root extract, or both.

5. The topical composition of claim 2, wherein the anti-acne herbal extract contains a Watercress extract, a witch hazel extract, a centella extract, a licorice extract, or a combination thereof.

6. The topical composition of claim 2 further contains a polysaccharide.

7. The topical composition of claim 2, wherein the composition contains L-fucose, D-galactose, galacturonic acid, or a combination thereof.

8. The topical composition of claim 2, wherein the anti-wrinkle herbal extract, the whiting herbal extract, and the anti-acne herbal extract are prepared at the w/w ratio of 3-30%, 3-30%, and 3-30%, respectively.

9. An isolated polypeptide comprising the sequence of SEQ ID NO: 1.

10. The isolated polypeptide of claim 9, wherein the polypeptide is SEQ ID NO: 1.

* * * * *

```
SEQUENCE LISTING

<160> NUMBER OF SEQ ID NOS: 2

<210> SEQ ID NO 1
<211> LENGTH: 89
<212> TYPE: PRT
<213> ORGANISM: Artificial Sequence
<220> FEATURE:
<223> OTHER INFORMATION: Naturally occurring peptide

<400> SEQUENCE: 1

Met Asn Ala Lys Val Val Val Leu Val Leu Val Leu Thr Ala Leu
 1               5                  10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
            35                  40                  45

Ile Leu Asn Thr Pro Asn Cys Ala Leu Gln Ile Val Ala Arg Leu Lys
        50                  55                  60

Asn Asn Asn Arg Gln Val Ser Ile Asp Pro Lys Leu Lys Trp Ile Gln
65                  70                  75                  80

Glu Tyr Leu Glu Lys Ala Leu Asn Lys
                85

<210> SEQ ID NO 2
<211> LENGTH: 270
<212> TYPE: DNA
<213> ORGANISM: Artificial Sequence
<220> FEATURE:
<223> OTHER INFORMATION: Naturally occurring oligonucleotide

<400> SEQUENCE: 2
atgaacgcca aggtcgtggt cgtgctggtc ctcgtgctga ccgcgctctg cctcagcgac      60
gggaagcccg tcagcctgag ctacagatgc ccatgccgat tcttcgaaag ccatgttgcc     120
agagccaacg tcaagcatct caaaattctc aacactccaa actgtgccct tcagattgta     180
```

```
gcccggctga agaacaacaa cagacaagtg tccattgacc cgaagctaaa gtggattcag      240
gagtacctgg agaaagcttt aaacaagtaa                                      270
```